United States Patent [19]
Mahoney

[11] Patent Number: 5,868,671
[45] Date of Patent: Feb. 9, 1999

[54] MULTIPLE ECG ELECTRODE STRIP

[75] Inventor: Steven A. Mahoney, McMinnville, Oreg.

[73] Assignee: Hewlett-Packard Company, Palo Alto, Calif.

[21] Appl. No.: 789,577

[22] Filed: Jan. 28, 1997

[51] Int. Cl.$^6$ ...................................................... A61B 5/408
[52] U.S. Cl. ........................... 600/382; 600/392; 600/393
[58] Field of Search ..................................... 600/382, 386, 600/388, 389, 350, 351, 352, 353; 607/145, 152, 153

[56] References Cited

U.S. PATENT DOCUMENTS

| | | |
|---|---|---|
| 3,476,104 | 11/1969 | Davis . |
| 4,033,333 | 7/1977 | DeSalvo et al. . |
| 4,121,575 | 10/1978 | Mills et al. . |
| 4,202,344 | 5/1980 | Mills et al. . |
| 4,233,987 | 11/1980 | Feingold . |
| 4,353,372 | 10/1982 | Ayer . |
| 4,583,549 | 4/1986 | Manoli . |
| 4,733,670 | 3/1988 | Hays et al. . |
| 4,832,608 | 5/1989 | Kroll . |
| 4,957,109 | 9/1990 | Groeger et al. . |
| 5,042,481 | 8/1991 | Suzuki et al. . |
| 5,168,875 | 12/1992 | Mitchiner . |
| 5,184,620 | 2/1993 | Cudahy et al. . |
| 5,191,886 | 3/1993 | Paeth et al. . |
| 5,224,479 | 7/1993 | Sekine . |
| 5,257,631 | 11/1993 | Wilk . |
| 5,327,888 | 7/1994 | Imran . |
| 5,341,806 | 8/1994 | Gadsby et al. . |
| 5,445,149 | 8/1995 | Rotolo et al. . |
| 5,507,290 | 4/1996 | Kelly et al. . |
| 5,678,545 | 10/1997 | Stratbucker .............................. 600/393 |

FOREIGN PATENT DOCUMENTS

WO 97 19631  6/1997  WIPO .

*Primary Examiner*—Lee S. Cohen

[57] ABSTRACT

A harness for placing on a patient's chest allows ECG measurements to be quickly made. The harness includes a strip of nonconductive film having a connector terminal at one edge for connection to an ECG measuring devise. The strip has a number of electrodes formed on it, each having leads extending to the connector terminal. At least some of the electrodes are grouped into sets. Each of the sets has a pattern of electrodes spaced for placement on a patient of a different size. Each of the electrodes within the sets has a corresponding electrode in another of the sets with which it is in electrical common. A backing layer may be peeled-off to expose the electrodes. The backing layer has separate zones, one for each of the sets of electrodes.

10 Claims, 2 Drawing Sheets

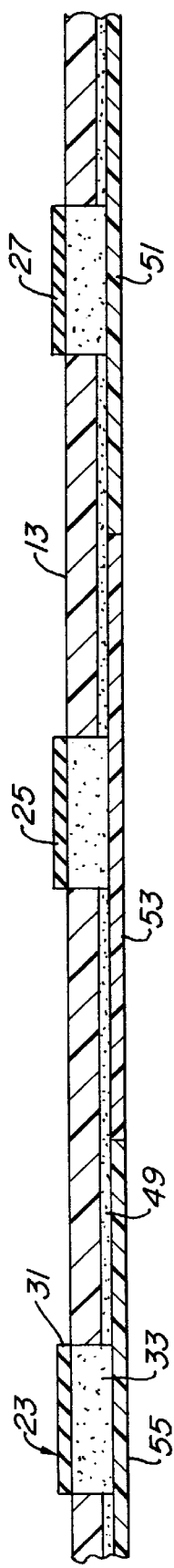
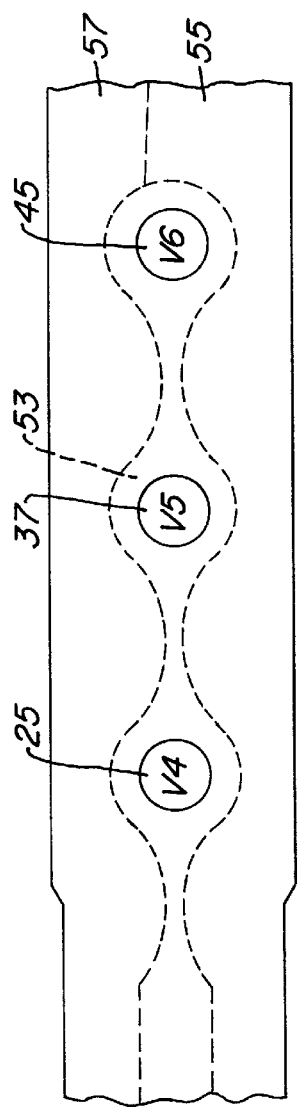

MULTIPLE ECG ELECTRODE STRIP

FIELD OF THE INVENTION

This invention relates generally to sensors for conducting electrocardiograph measurements, and in particular to a harness that facilitates rapid and proper placement of the electrodes on a patient.

BACKGROUND OF THE INVENTION

Electrocardiograph measurements ("ECG") are commonly made to provide information about a patient's heart performance. Typically a technician will place sensors on a patient's chest. The sensors are electrodes having an adhesive gel for adhering to the skin of the patient as well as for providing electrical conductivity. The technician then clips leads from an ECG monitor to a terminal on each of electrode pads. The technician will monitor voltage differential to provide a chart indicating the condition of the patient's heart.

It is important to place the electrode pads at fairly precise anatomical positions. These positions have been established so as to provide adequate comparisons with ECG measurements that have been taken across a wide variety of patients. However, varieties in patient size makes this placement a difficult task. Normally, six of the electrode pads must be positioned, then clipped to the leads. Furthermore, the technician has to be careful to clip the proper leads to the proper electrode pads.

Skill and care are required to be able to properly position the sensors for an ECG measurement. This become a more difficult task during emergencies. For example, ECG measurements made in an ambulance or with a portable ECG device at a field site are very informative. With time of the essence, it is a difficult task to properly and quickly place and connect the electrode pads.

Prior art patents show a variety of devices for facilitating ECG measurements. Generally these devices include some type of strip or harness with the electrodes being prewired to a connector terminal on an edge of the strip. Preconnecting the electrode pads to a connector terminal reduces the chances for a technician to switch the leads inadvertently. Also, some of the devices place the electrodes in the general vicinity of the desired anatomical position. However, because of the differences in patient size, a variety of sizes of these strips may need to be kept on hand. Some of the devices shown would appear to be expensive. For one reason or another, such prewired strips are not commonly used.

SUMMARY OF THE INVENTION

In this invention, a harness or strip is employed for placement on the chest of a patient. The strip is of a nonconductive film and has a connector terminal on one edge for to an ECG measuring devise. A plurality of leads or traces are formed in the film and extend from the connector terminal. The leads join the connector terminal with electrodes which are formed in the strip for contact with the patient's skin. Some of the electrodes are connected to the same leads but spaced apart from each other on the strip for placement on patients of different sizes. An adhesive layer is located on the back side for adhering to a patient's chest. A backing layer covers the adhesive layer and the electrodes.

The backing layer is divided into separate peel-off zones. Some of the zones cover sets of electrodes, with each set being a pattern for a particular patient size. A technician may select and remove certain ones of the zones and retain others. Partial removal of the zones exposes only some of the electrodes while covering others. The electrodes selected to be exposed are the ones that best fit the particular patient. This allows the strip to be used for patients of different sizes.

BRIEF DESCRIPTION OF THE DRAWINGS

FIG. 2 is an enlarged sectional view of the harness of FIG. 1, taken along the line 2—2 of FIG. 1, and exaggerated in thickness.

FIG. 3 is a partial elevational view of the back side of the harness of FIG. 1, and showing the medium zone of the backing layer removed.

DETAILED DESCRIPTION OF THE PREFERRED EMBODIMENT

Figure 1:
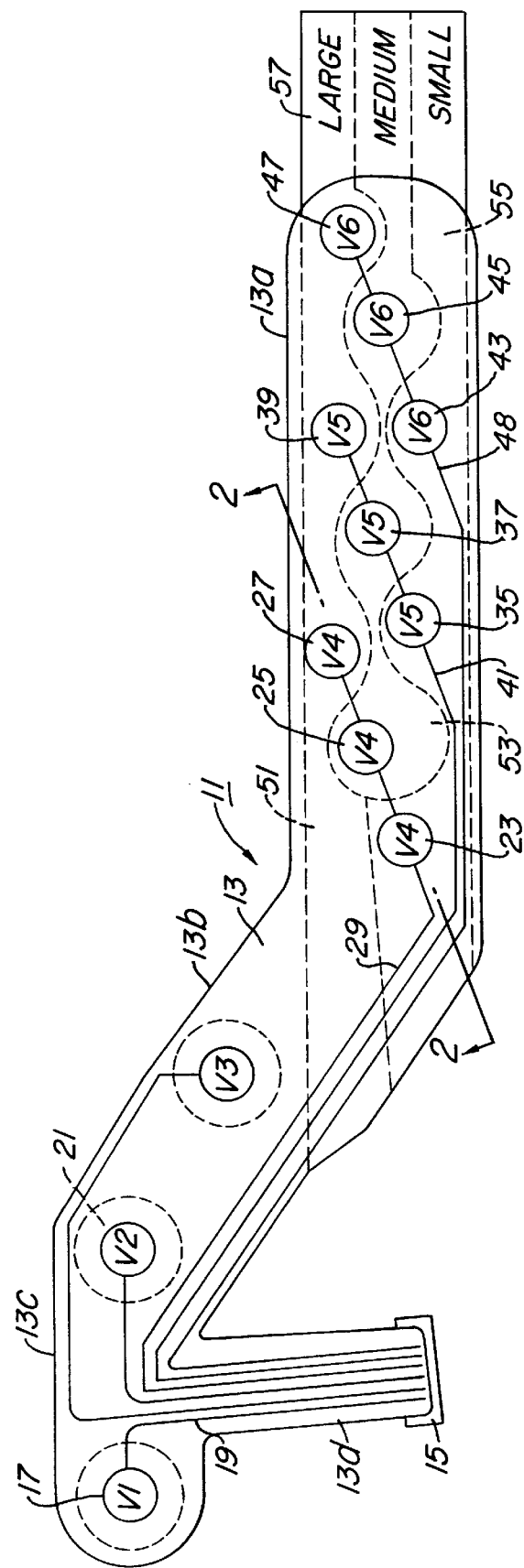
FIG. 1 is an elevational view, partially schematic, illustrating an ECG harness constructed in accordance with this invention.

Referring to FIG. 1, harness 11 is an elongated flexible apparatus for placement on ECG patients. Harness 11 includes a strip 13 of a nonconductive, thin and flexible film. Strip 13 has a lateral portion 13a which joins a diagonal portion 13b. Diagonal portion 13b joins a head portion 13c. A terminal portion 13d extends from head portion 13c at a 90° angle relative to head portion 13c. Terminal portion 13d includes a connector terminal 15 on its end which is shown schematically and is adapted to connect to a connector of an ECG monitor.

In the embodiment shown, there are three electrodes 17, which are also designated by the letters V1, V2 and V3. Electrodes 17 are the three electrodes located the closest to terminal portion 13d. Measurements have shown that regardless of the size of a patient's chest, electrodes 17 will be in the approximate desired anatomical position. A separate lead 19 extends from connector terminal 13d to each electrode 17. Leads 19 are of a conductive ink, such as silver/silver chloride, screen printed on strip 13. Each electrode 17 is isolated electrically from the other electrodes 17. A nonconductive backing layer 21 is secured to the back side of strip 13 to prevent exposure of electrodes 17 until backing layer 21 is peeled off. In the embodiment shown, backing layer 21 comprises three separate peel-off circular pieces, each one covering one of the electrodes 17.

A plurality of additional electrodes are also located on strip 13, generally in the lateral portion 13a. These electrodes include three V4 electrodes 23, 25 and 27. Each inner electrode 23, 25, 27 is electrically connected together by the same V4 lead 29 which leads back to connector terminal 15. The three V4 electrodes 23, 25, 27 are spaced at different distances from connector terminal 15. Electrode 23 is closer to terminal portion 13d than electrode 25, which is in turn is closer than electrode 27.

Referring to FIG. 2, electrode 23 includes a conductive film 31 and a conductive gel 33 on the back side of film 31. Film 31 is preferably made conductive by screen printing a conductive ink such as silver/silver chloride on strip 13. It will be formed in the same manner as lead 29. Conductive gel 33 is preferably also an adhesive for adhering to a patient's skin. A nonconductive coating (not shown) will cover the front side of electrode 31 as well as lead 19. Electrodes 17, as well as all the other electrodes, are constructed in the same manner as electrode 23.

Similarly, three V5 electrodes 35, 37 and 39 are located on strip 13. Intermediate electrodes 35, 37, 39 are all spaced farther from terminal 15 than inner electrodes 23, 25, 27.

Electrode 35 is spaced closer to terminal 15 than electrode 37, which in turn is closer than electrode 39. Intermediate electrodes 35, 37, 39 are all connected to the same lead 41 that extends back to connector terminal 15.

In the same manner three V6 electrodes 43, 45, 47 are formed on strip 13, farther outward than intermediate electrodes 35, 37 and 39. Electrode 43 is closer to terminal 15 than electrode 45, which in turn is closer than electrode 47. Outer electrodes 43, 45, 47 are each connected to a single lead 48 that extends to connector terminal 15.

Referring again to FIG. 2, the back side of strip 13 is coated with an adhesive layer 49 which surrounds the conductive gel 33. A backing layer encloses adhesive layer 49 until use. The backing layer is a peel-off type and has three segments or zones 51, 53 and 55 shown also in FIG. 1. Large patient size zone 51 encompasses one set of electrodes, the set comprising V4 electrode 27, V5 electrode 39, and V6 electrode 47. A pull-tab 57 enables large zone backing layer 51 to be peeled-off, exposing only the three electrodes 27, 39 and 47 of the large set.

Similarly medium patient size zone 53 covers only a set comprising electrodes 25, 37 and 45. It too has a tab 57, which enables pulling-off medium zone layer 53, as shown in FIG. 3. Small patient size zone backing layer 55 covers only a set of electrodes 23, 35 and 43. It may be peeled-off to expose these electrodes without exposing any of the other sets of electrodes. Each set of electrodes includes one inner V4 electrode 23, 25, or 27, one intermediate V5 electrode 37, 39, or 41, and one outer V6 electrode 43, 45, or 47. The other three electrodes used for each patient regardless of size are the isolated V1, V2, and V3 electrodes 17.

In use, the technician will inspect the patient to determine the proper size. If the patient is of a medium size, the technician will pull-off medium zone backing layer 53 and each of the backing layers 21. This exposes the V1, V2 and V3 electrodes 17 and exposes the medium set of electrodes 25, 37 and 45. These electrodes are approximately positioned for a medium size patient. The user then places strip 13 on the chest of the patient, with adhesive layer 49 and gel 33 retaining strip 13 in place. The user connects connector terminal 13 to a monitor and conducts the ECG measurement. Normally harness 11 will be disposed of after each use. The same procedure would be followed for large and small patients, removing either backing layer 51 or backing layer 55.

The invention has significant advantages. It allows a technician to quickly prepare a patient for an ECG measurement. It avoids switching leads and improper placement of electrodes. The alternate electrodes allow a single strip to be used for a variety of patient sizes, reducing inventory costs.

I claim:

1. An apparatus for placing on a patient's chest for making ECG measurements, comprising:
    a strip of nonconductive film having a connector terminal at one edge for connection to an ECG measuring device;
    a plurality of leads formed in the film and extending from the connector terminal;
    a first set of electrodes on the strip and spaced in an array for contact with skin of a patient of a first size range, each of the electrodes of the first set being electrically connected to a separate one of the leads;
    a second set of electrodes on the strip and spaced in an array for contact with skin of a patient of a second size range, each of the electrodes of the second set being electrically connected to a separate one of the leads;
    at least some of the electrodes in the first set being electrically connected to the same leads as corresponding ones of the electrodes in the second set and spaced from said corresponding ones for placement on patients of different sizes; and
    a backing layer covering a back side of the strip and the electrodes, the backing layer being divided into separate peel-off zones, whereby a technician may selectively remove certain of the zones and retain other of the zones, to expose only the electrodes for a selected patient size range.

2. The apparatus according to claim 1, wherein one of the zones of the backing layer covers the first set of electrodes, and another one of the zones of the backing layer covers the second set of electrodes.

3. The apparatus according to claim 1, wherein each of the electrodes in the first set is electrically connected to the same lead as one of the electrodes in the second set; and wherein the apparatus further comprises:
    a plurality of isolated electrodes on the strip for contact with skin of a patient, each of the isolated electrodes being connected to a separate one of the leads.

4. The apparatus according to claim 1, further comprising a third set of electrodes on the strip and spaced in an array for contact with skin of a patient of a third size range, each of the electrodes of the third set being electrically connected to a separate one of the leads and being electrically connected to one of the electrodes of the first set and one of the electrodes of the second set.

5. The apparatus according to claim 1, further comprising an adhesive layer on the back side of the strip for adhering to a patient's chest, the adhesive layer being covered by the backing layer until use.

6. An apparatus for placing on a patient's chest for making ECG measurements, comprising:
    a strip of nonconductive film having a connector terminal at one edge for connection to an ECG measuring device;
    a plurality of electrodes formed on the strip;
    a plurality of leads formed in the strip and extending from the electrodes to the connector terminal;
    at least some of the electrodes being grouped into sets of electrodes, each of the sets having a pattern of the electrodes spaced for placement on a patient of a different size, each of the electrodes within the sets having a corresponding one of the electrodes within another one of the sets with which it is electrically in common;
    an adhesive layer on a back side of the strip for adhering to a patient's chest; and
    a backing layer covering the adhesive layer and the electrodes, the backing layer including a plurality of separate peel-off zones, one for each of the sets of electrodes, whereby a technician may selectively remove one of the zones for exposing one of the sets of electrodes for a patient of one size and remove another one of the zones for exposing another one of the sets of electrodes for a patient of a different size.

7. The apparatus according to claim 6 wherein each of the sets of electrodes has an outer electrode and an inner electrode, the outer electrodes of the sets corresponding with and being electrically common with one another, the inner electrodes of the sets corresponding with and being electrically common with one another, the outer electrode of each of the sets being spaced farther from the connector terminal than the inner electrode of the same one of the sets.

8. The apparatus according to claim 6 wherein each of the sets of electrodes has an outer electrode, an intermediate electrode, and an inner electrode, the outer electrodes of the sets corresponding with and being electrically common with one another, the intermediate electrodes of the sets corresponding with and being electrically common with one another, the inner electrodes of the sets corresponding with and being electrically common with one another, the outer, intermediate and inner electrodes of one of the sets being spaced closer to the terminal than the outer, intermediate and inner electrodes of another of the sets, respectively.

9. The apparatus according to claim 6 wherein a plurality of the electrodes are isolated electrodes for placement on a patient regardless of patient size, each of the isolated electrodes being connected to a separate one of the leads.

10. A method for placing ECG sensors on a patient's chest, comprising:

providing a strip of nonconductive film with a connector terminal at one edge, a plurality of leads formed in the film and extending from the connector terminal, and a plurality of electrodes secured to the strip and electrically connected to the leads, with some of the electrodes being in sets with different patterns for different patient sizes, each of the electrodes in each of the sets having a corresponding electrode in another of the sets with which it is electrically in common;

providing a backing layer which covers the electrodes, the backing layer being divided into separate peel-off portions;

connecting the terminal to an ECG monitor; and based on patient size, selectively removing portions of the backing layer to expose one of the sets of electrodes while retaining the backing layer over the other of the sets, and placing the strip on the patient.

* * * * *